(12) United States Patent
Zen et al.

(10) Patent No.: US 7,438,853 B2
(45) Date of Patent: Oct. 21, 2008

(54) PHOTOELECTROCATALYTIC METHOD AND PHOTOELECTROCHEMICAL DETECTOR FOR ELECTROCHEMICAL ANALYSIS

(75) Inventors: Jyh-Myng Zen, No. 169, Tali 2 St., Tali City, Taichung Hsien (TW); Hsieh-Hsun Chung, Tali (TW); Cheng-Teng Hsu, Tali (TW); Hsueh-Hui Yang, Tali (TW); Mei-Shin Chiou, Tali (TW); Jun-Wei Sue, Tali (TW)

(73) Assignee: Jyh-Myng Zen (TW)

( * ) Notice: Subject to any disclaimer, the term of this patent is extended or adjusted under 35 U.S.C. 154(b) by 962 days.

(21) Appl. No.: 10/848,373

(22) Filed: May 19, 2004

(65) Prior Publication Data

US 2005/0258816 A1 Nov. 24, 2005

(51) Int. Cl.
*G01N 27/00* (2006.01)
*G01N 27/26* (2006.01)
*G01N 25/08* (2006.01)
*G01N 21/76* (2006.01)

(52) U.S. Cl. .................. 422/82.01; 422/52; 422/55; 422/82.05; 422/82.07; 204/400; 204/229.1; 204/228.9; 204/229.9; 250/361 C; 436/150; 436/172

(58) Field of Classification Search .................. None
See application file for complete search history.

(56) References Cited

U.S. PATENT DOCUMENTS 6,200,531 B1 * 3/2001 Liljestrand et al. ............ 422/52

* cited by examiner

*Primary Examiner*—Jill Warden
*Assistant Examiner*—Neil Turk
(74) *Attorney, Agent, or Firm*—Hershkovitz & Associates, LLC; Abe Hershkovitz

(57) ABSTRACT

A photoelectrocatalytic method for detecting current that illuminates a photoelectrochemical electrode to generate a photocurrent and to magnify the current. Thereby, accuracy of the detection is increased. A photoelectrochemical detector used in the method has a base (10), a cover (20) pivotally mounted on the base (10) and a locking device attached between the base (10) and the cover (20). The base (10) has a top and a recess (12) defined in the top to accommodate a working electrode (50) with a photoelectrochemical inner lead (52). A spacer is clamped between the base (10) and the cover (20) to form a space over the inner lead (52). Multiple channels and a light hole (22) are defined through the cover (20) to communicate with the space. Therefore, the inner lead is illuminated through the light hole (22) to perform the photoelectrochemical method.

10 Claims, 6 Drawing Sheets

(A)

(B)

PHOTOELECTROCATALYTIC METHOD AND PHOTOELECTROCHEMICAL DETECTOR FOR ELECTROCHEMICAL ANALYSIS

BACKGROUND OF THE INVENTION

1. Field of the Invention

The present invention relates to a photoelectrocatalytic method and photoelectrochemical detector and more particularly to that use copper-plate screen-printed carbon electrode (designated CUSPE) to increase the sensitivity in electrochemical detection.

2. Description of Related Art

Electrochemical detectors are widely used in various fields of science and technology. Good detecting devices need to have excellent selectivity, sensitivity, short response time and further have excellent stability and reliability. Electrochemical detector can be used with flow injection analysis (FIA), high performance liquid chromatography (HPLC), or capillary electrophoresis (CE).

The present invention provides a photoelectrocatalytic method as well as a photoelectrochemical detector to increase the sensitivity in electrochemical detection over conventional electrochemical detectors.

SUMMARY OF THE INVENTION

One objective of the present invention is to provide a photoelectrocatalytic method to increase the sensitivity in electrochemical detection.

A second objective of the present invention is to provide a detecting device to perform the foregoing method conveniently with various electrodes in different systems.

Further benefits and advantages of the present invention will become apparent after a careful reading of the detailed description with appropriate reference to the accompanying drawings.

APPENDIX

*Analytical Chemistry*, 7020-7025, vol. 75 No 24 Dec. 15, 2003.

DETAILED DESCRIPTION OF THE PREFERRED EMBODIMENT

A photoelectrocatalytic method for detecting current in accordance with the present invention uses light to illuminate electrodes to increase the sensitivity so as to increase the accuracy of detection.

The electrode can be copper, silver, gold and an alloy or derivatives from these metals. When a cupriferous alloy is selected, the material is preferred to be a copper-platinum alloy, copper-palladium alloy, copper-mercury alloy, copper-silver alloy, copper-gold alloy, etc. When a cupriferous derivative is selected, the material is preferred to be cupric chloride ($CuCl_2$), cupric bromide ($CuBr_2$), cupric iodide ($CuI_2$), cupric oxide (CuO), cupric fluoride ($CuF_2$), cupric astatine (CuAt), cuprous oxide ($Cu_2O$), etc. Cupric oxide (CuO) and cuprous oxide ($CU_2O$) are the optimal materials in the present invention. A description of the mechanics of using cupric oxide and cuprous oxide is illustrated as the followings.

Cupric oxide and cuprous oxide are semiconductor material and possess photoelectrochemical properties and are used mostly as CuSPE. Cuprous oxide is a p-type semiconductor material with a band gap of approximately 1.5 to 2.0 eV and a light-absorbing wavelength within 500 to 600 nm. The CuSPE made of cupreous oxide has the following reacting mechanism:

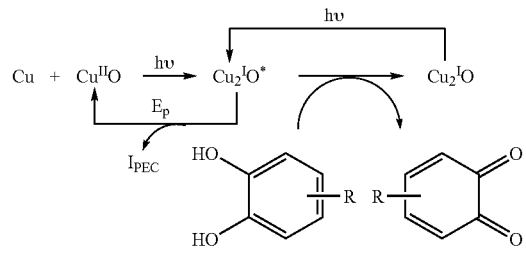

When the Cu and $Cu^{II}O$ are illuminated with light, the Cu and $Cu^{II}$ absorb light energy, and are stimulated to become activated $Cu_2^IO^*$. When illuminated with light, photoelectrochemical current ($I_{PEC}$) is generated because $Cu^{II}O$ and $Cu_2^IO^*$ have different electric potential ($E_p$). When electron donors such as catechol is used with the detecting device having photoelectrochemical material electrodes, the activated $Cu_2^IO^*$ takes electrons and returns to $Cu_2^IO$. Therefore, the generated photoelectrochemical current from the transition between $Cu_2^IO^*$ and $Cu_2^IO$ significantly magnifies the total current in detection.

Figure 1:
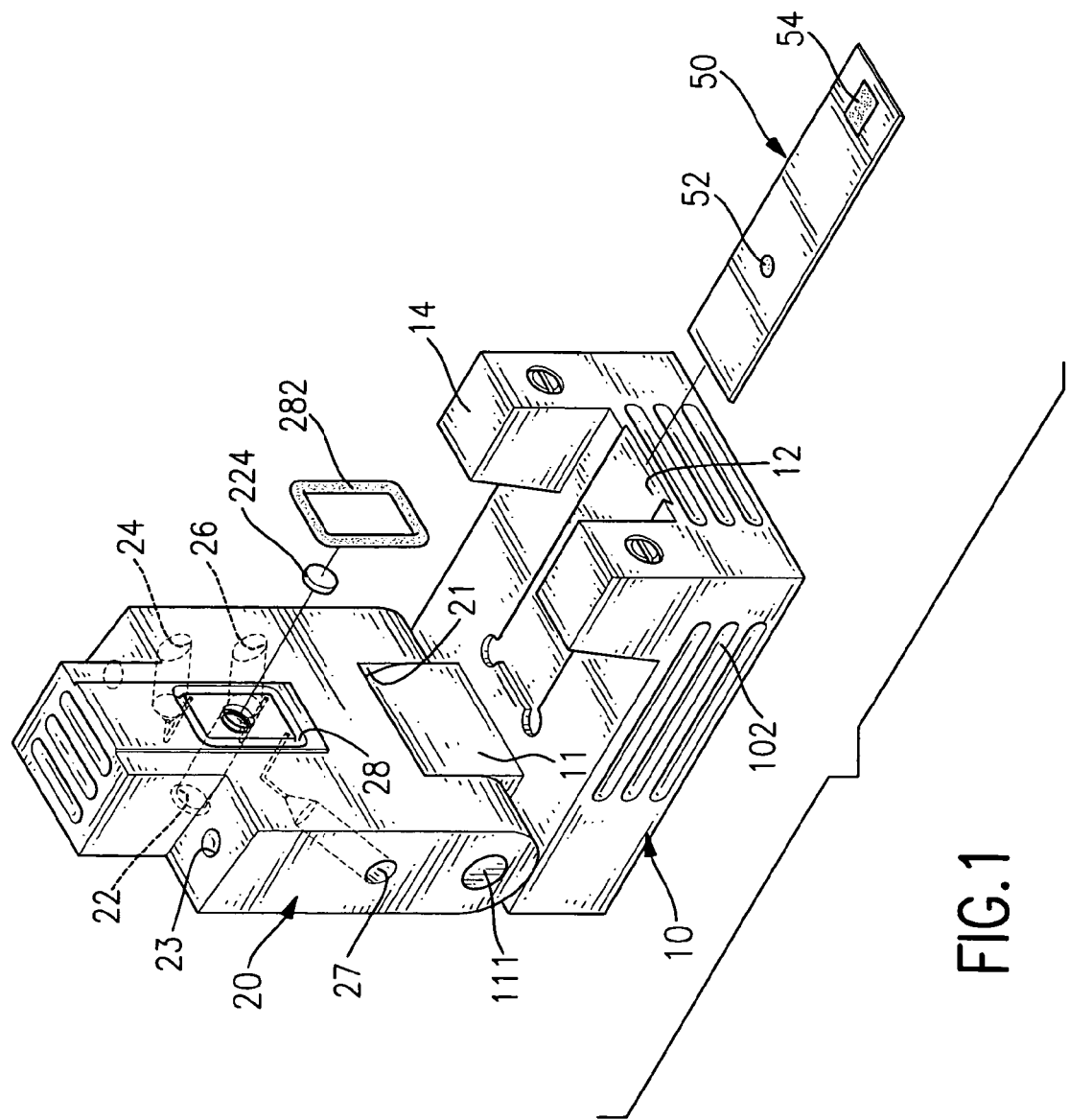
FIG. 1 is a perspective view of a photoelectrochemical detector used with a photoelectrocatalytic method to detect current in accordance with the present invention.
Figure 2:
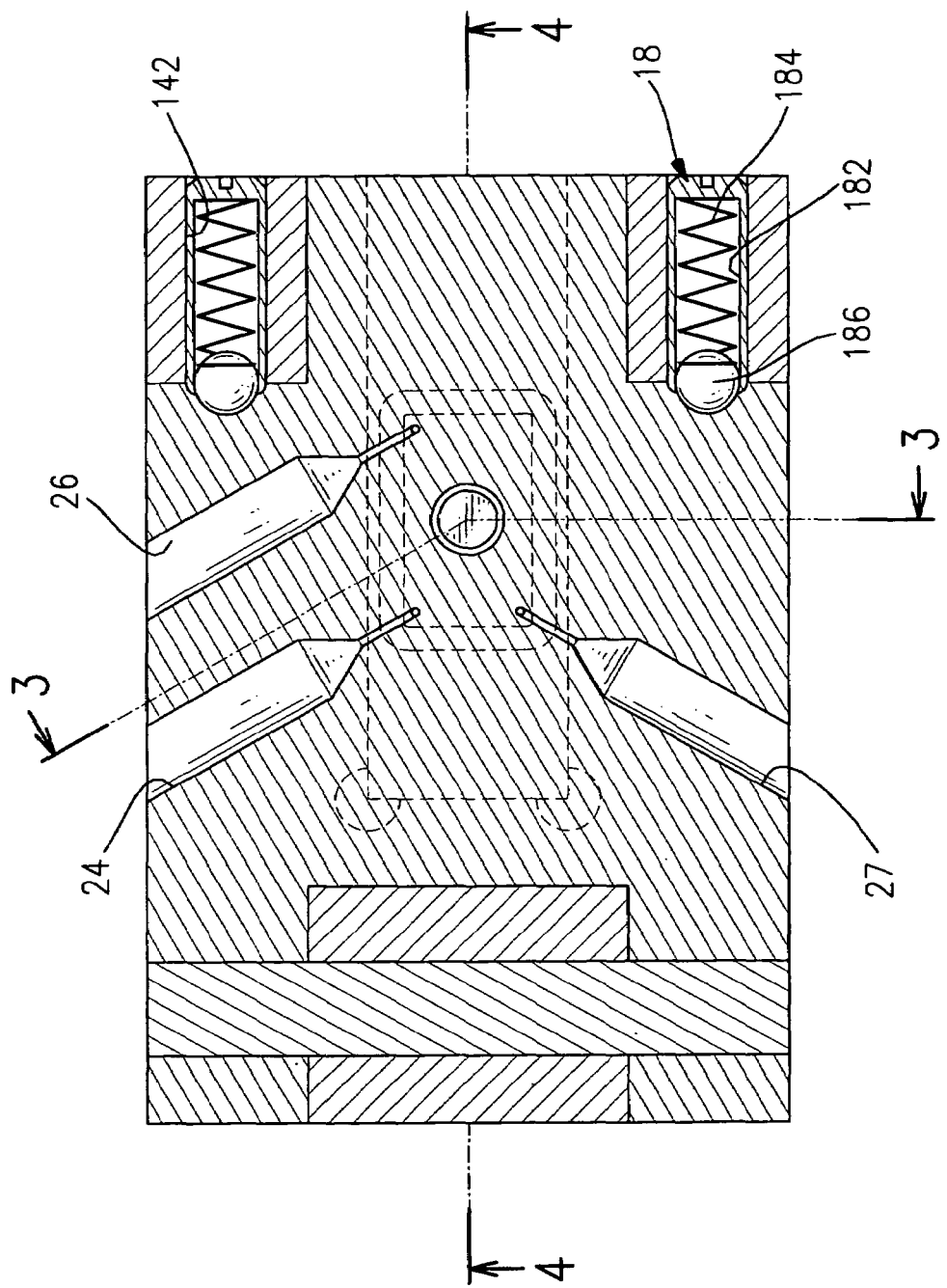
FIG. 2 is a cross-sectional top plane view of the detecting device in FIG. 1 with the detecting device closed.

With reference to FIGS. 1 and 2, a photoelectrocatalytic detecting device in accordance with the present invention comprises a body (10), a cover (20), a replaceable working electrode (50) and a locking device (not numbered). The replaceable working electrode (50) is made of material with photoelectrochemical property. The locking device is mounted between the base (10) and the cover (20).

The base (10) is a rectangular parallelepiped and has a top (not numbered), two sides (not numbered), a front end (not numbered), a rear end (not numbered), a recess (12), a pivot post (11) and multiple optional anti-slip grooves (102). The recess (12) is defined longitudinally in the top and extends to the front end, and the pivot post (11) is formed on the top near the rear end. The optional anti-slip grooves (102) are defined in the sides and front and rear ends to make holding the base (10) easy. The recess (12) is preferably a dovetail recess to prevent the working electrode (50) inside the recess (12) from detaching from the top when the working electrode (50) is attached to the cover (20).

Figure 3:
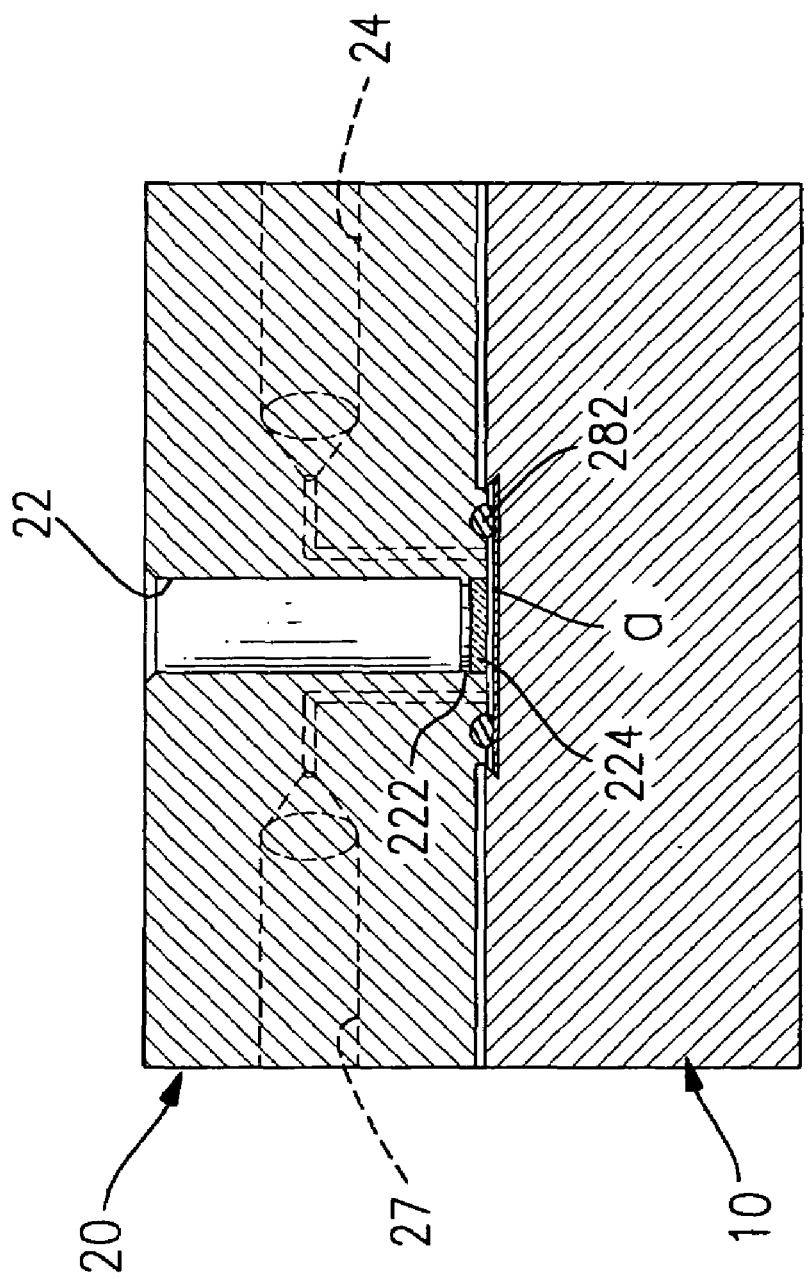
FIG. 3 is a cross-sectional front plane view of the detecting device along line 3-3 in FIG. 2.

The cover (20) is attached pivotally to the top of the base (10), is also a substantially rectangular parallelepiped and has a top (not numbered), a bottom (not numbered), a front end (not numbered), a rear end (not numbered), two sides (not numbered), two side cutouts (not numbered), a spacer (not numbered), multiple channels (24, 26, 27), a light hole (22), a hinge recess (21) and a pivot pin (111). The two side cutouts are defined on opposite sides of the front end. The spacer (not numbered) has a gasket seat (28), a gasket (282) and an inner open area (not numbered). The gasket seat (28) is rectangular and is defined in the bottom of the cover (20). The gasket (282) is rectangular, is mounted in the gasket seat (28) and seals off the inner open area when the cover (20) is closed. With further reference to FIG. 3, the rectangular gasket (282) defines a space (a) between the base (10) and the cover (20) when the cover (20) is pressed downward and the rectangular gasket (282) fully abuts the base (10). The multiple channels (24, 26, 27) are defined in the cover (20), communicate between the inner open area in the spacer and the sides of the cover (20) and comprise a first outlet (24), a second outlet (26) and an inlet (27). The outlets (24, 26) and the inlet (27) are defined in opposite sides of the cover (20). The light hole (22) is defined through the cover (20) from the top to the bottom at the inner open area within the gasket seat (28) and has an inside end (not numbered), a window flange (222) and a window (224). The window flange (222) is formed near the inside end of the light hole (22) and protrudes radially inward. The window (224) is mounted in the light hole (22) against the window flange (222) and is flush with the inner open area of the spacer. The hinge recess (21) is defined in the rear end of the cover (20), and the pivot post (11) of the base (10) is mounted in the hinge recess (21). The pivot pin (111) is mounted transversely in the cover (20) through the hinge recess (21) and the pivot post (11) to pivotally attach the cover (20) to the base (10).

The locking device comprises two locking posts (14), two ball-spring combinations (not numbered) and two detents (23) and is attached between the base (10) and the cover (20) to hold the detecting device tightly closed. The two locking posts (14) protrude from the top of the base (10) at the front end, correspond to the side cutouts in the cover (20) and respectively have ball-spring combinations and holes (not numbered). Each ball-spring combination comprises a retractable ball (186), a resilient member (184) and an optional threaded rod (18), which are mounted in the holes in the locking posts (14). When the threaded rods (18) are mounted in the holes, the holes are threaded holes (142) and the threaded rods (18) screw into the threaded holes (142). The threaded rod (18) has a bore (182) defined axially to receive the retractable ball (186) and the resilient element (184). The resilient element (184) provides a restitution force to the ball (186) to push the ball (186) to detachably engage the ball detent (23). By adjusting a depth of the threaded rod (18) going into the threaded hole (142), the tightness degree of the locking device is adjustable. Preferably, the resilient element (184) is a spring. The detents (23) are defined respectively in the side cutouts in the cover (20) and are aligned respectively with the retractable balls (186) in the locking posts (14). Preferably, each locking post (14) has a threaded hole (142) defined in the locking post (14) and has one corresponding threaded rod (18) screwing into the threaded hole (142). The cover (20) is opened by pulling the cover (20) upward and disengaging the ball (186) from the ball detent (23) by forcing the ball (186) slightly into the hole. Therefore, the cover (20) is easily closed or opened in a convenient way by just applying a light pressure to the cover (20).

Figure 4:
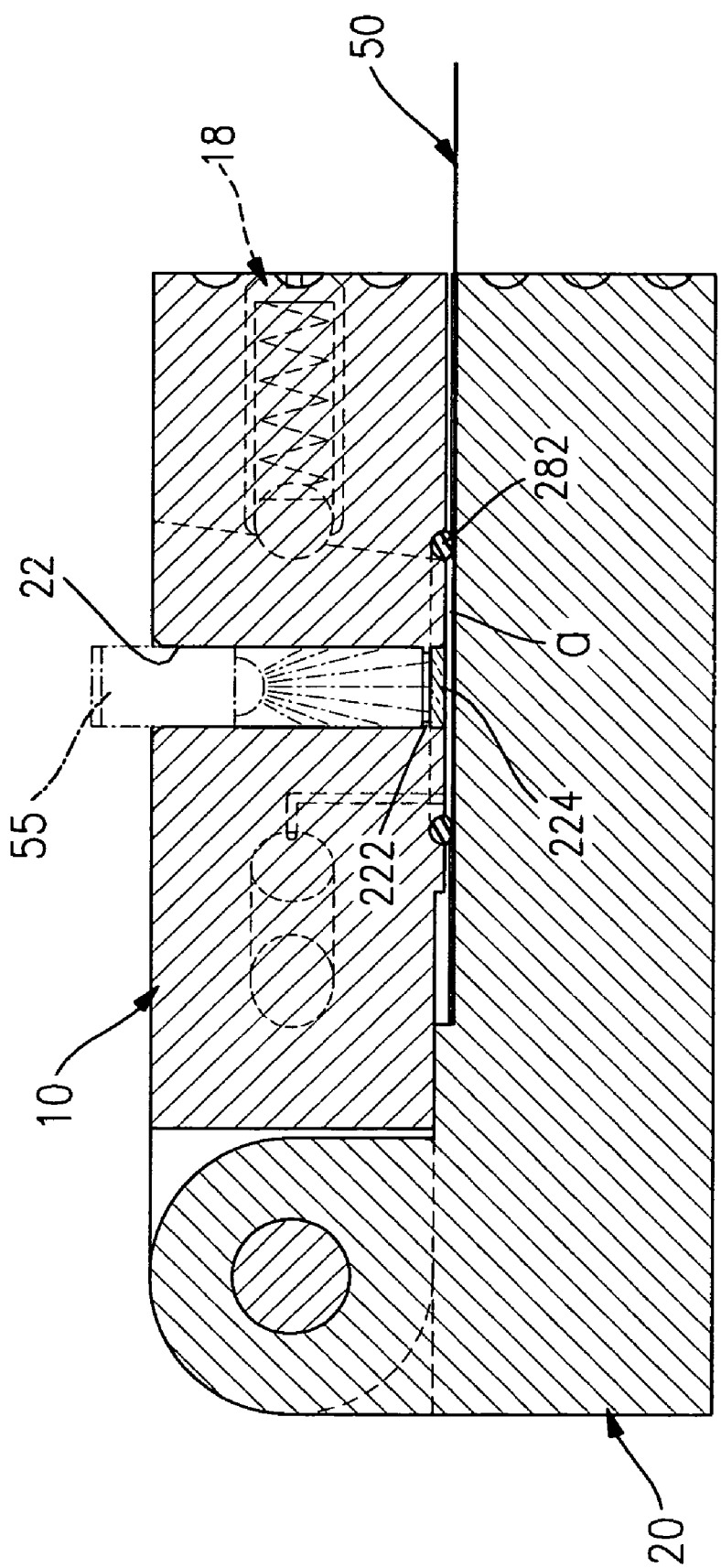
FIG. 4 is a cross-sectional side plane view of the detecting device along line 4-4 in FIG. 2.

With further reference to FIG. 4, the working electrode (50) has a top face (not numbered), an inner end (not numbered), an outer end (not numbered), an inner lead (52) and an outer lead (54) and is mounted in the recess (12). The outer end protrudes from the recess (12). The inner lead (52) is attached to the top face, aligns with the light hole (22) when the cover (20) is closed and is coated with photoelectrochemical material such as cupreous oxide. The outer lead (54) is attached to the top face at the outer end to connect electrically to a readout system (not shown).

With further reference to FIG. 4, the detecting device needs other accessories when the device operates. After closing the cover (20), fluid to be tested is injected into the space (a) through the inlet (27) and drained out through the first outlet (24) or the second outlet (26). When the detecting device operates, the working electrode (50) connects to an electricity source, and a light source (55) is attached to the cover (20) to illuminate the fluid through the light hole (22). Thereby, the inner lead (52) is activated and generates extra current to magnify the detected current in the fluid.

Additionally, the accessories comprise a reference electrode (not shown) and an auxiliary electrode (not shown) selectively attached to the first outlet (24) or the second outlet (26) to perform a double-check.

To operationally verify the photoelectrocatalytic method for detecting current using the detecting device in accordance with the present invention, an experiment to test o-phenols was performed to estimate the magnifying efficiency with regard to different light intensities.

Figure 5:
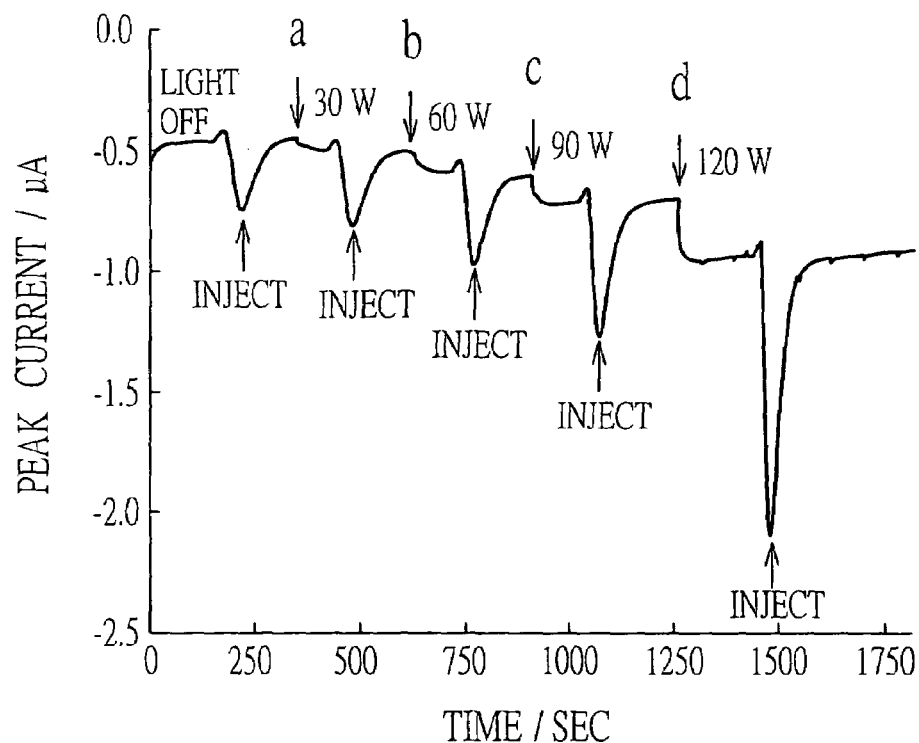
FIGS. 5(A) and 5(B) are an amperometric response diagrams under electrode irradiation in response to various intensities and a percentage bar chart showing increases in peak current.
Figure 5:
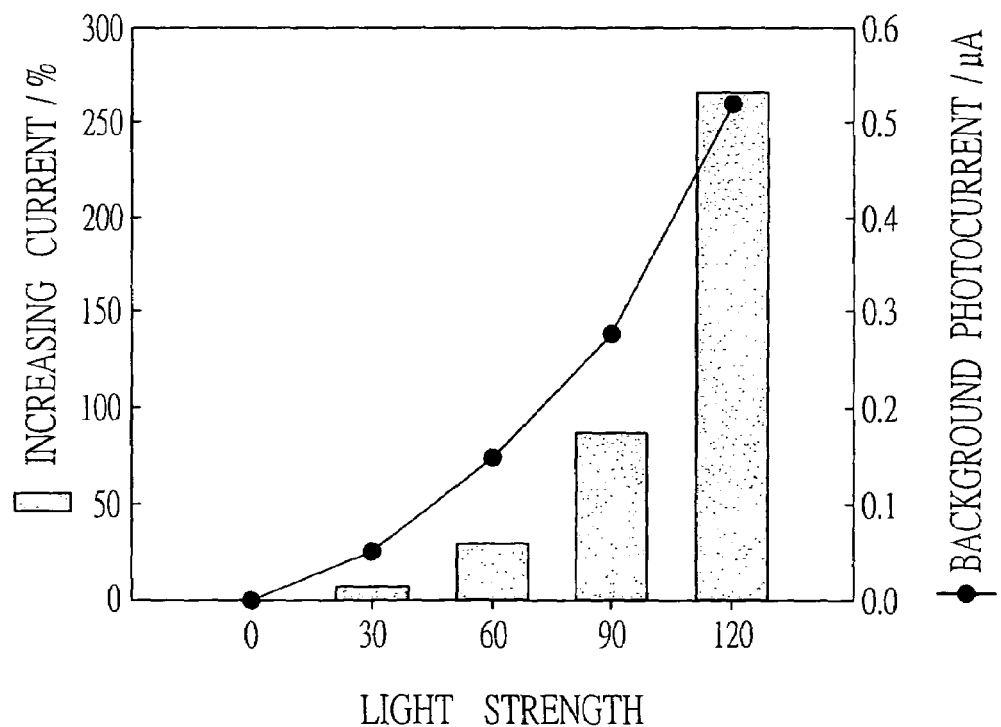
Figure 6:
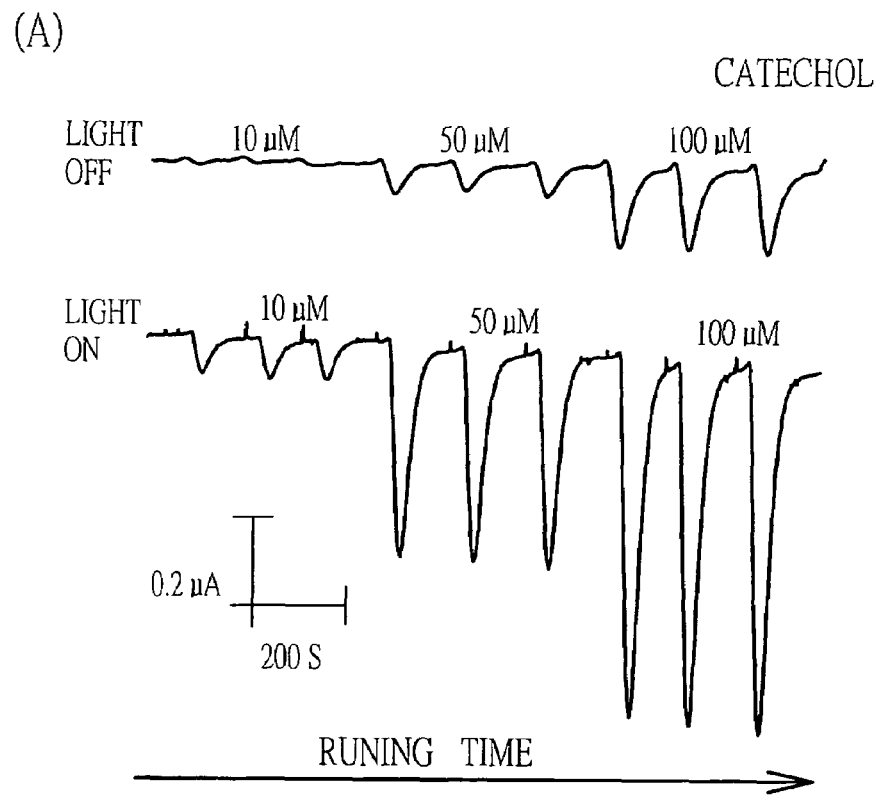
FIGS. 6(A) and 6(B) are an amperometric response diagrams at concentrations of 10, 50 and 100 μm and a calibration curve corresponding to the amperometric response diagram.
Figure 6:
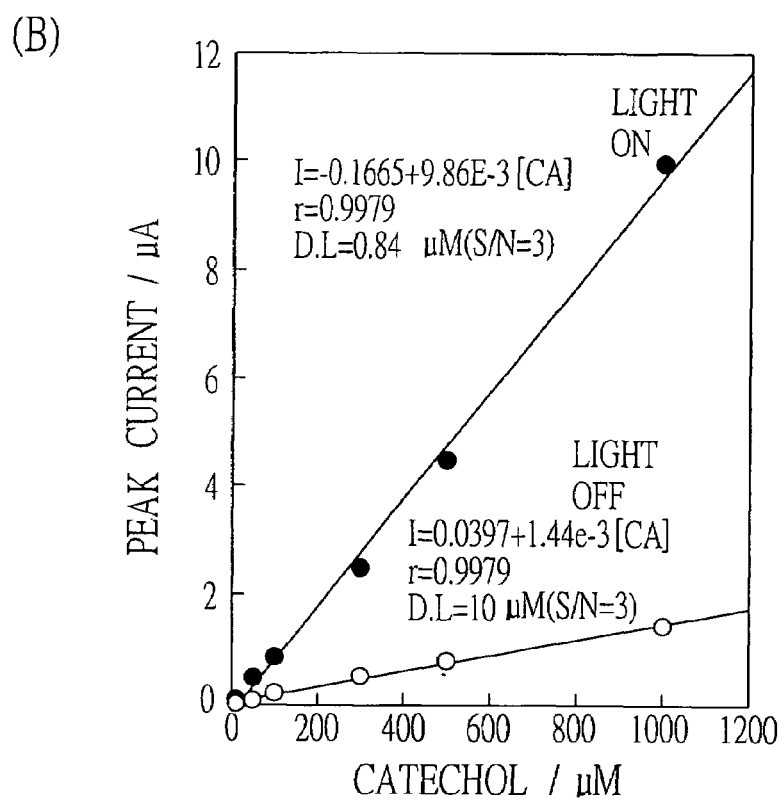

With reference to FIG. 5, o-phenol was illuminated with a 150 W halogen lamp. After 300 seconds, 100 $\mu$M of catechol was injected into the testing device and a 0.33 $\mu$A current was applied to the testing device without illumination. After 300 sec, light intensities were changed and gradually increased (on $-a$, $-b$, $-c$ and max. $-d$) in different time periods. In each time period, 100 $\mu$M of catechol was injected into the detecting device. The background photocurrent grew stronger when the light intensity increased, which proves the photoelectrochemical mechanism previously described. The background photocurrent is formed by an induced current of electrons that were obtained from the valence band. With further reference to FIG. 6, current signals of catechol were also increased with the growth of the background photocurrent. However, extreme limits were not obtained in this experiment. The 150 W halogen lamp magnified the detected current of catechol by 267%, and the amplified current was not overloaded. Using more powerful illumination to increase the sensitivity of the detecting current is a reasonable assumption.

The present invention has been examined by American Chemical Society and been published on 7020-7025 vol. 75 No 24 Dec. 15, 2003, Analytical Chemistry. (see the attached appendix)

According to the foregoing experiment and description, the photoelectrocatalytic method significantly magnifies the current to increase the sensitivity of the detection. Furthermore, the detecting device is easily operated since the cover (20) pivotally detaches from or engages the base (10). Therefore, the working electrode (50) can be changed in a convenient way.

Although the invention has been explained in relation to multiple preferred embodiments, many other possible modifications and variations can be made without departing from the spirit and scope of the invention as hereinafter claimed.

What is claimed is:

1. A photoelectrochemical detector comprising:
a base (10) with a top, a front end, a rear end and sides, and having a recess (12) defined longitudinally in the top and extending to the front end;
a cover (20) with a top, a bottom, a front end, a rear end and two sides, which is mounted pivotally on the base (10) and has a spacer with an inner open area attached to the bottom of the cover (20), and a light hole (22) and multiple channels defined through the cover (20) to communicate with the inner open area of the spacer, wherein a light source (55) is attached to the cover (20) to operatively communicate with light hole (22);
a working electrode (50) mounted in the recess (12) and having a top face, an inner end, an outer end, and an inner lead (52) made of material with photoelectrochemical properties, wherein the inner lead (52) is attached on the top face of the working electrode (50) near the inner end and aligned with the light hole (22) when the cover (20) is closed, and wherein the working electrode is connected to an electricity source; and
wherein the multiple channels are:
an inlet (27) defined in the cover (20) on one side;
a first outlet (24) defined in the cover (20) on the other side; and
a second outlet (26) defined in the cover (20) on the same side as the first outlet (24); and
wherein the device further has a reference electrode (30) corresponding to the first outlet (24); and
wherein the device further has an auxiliary electrode (40) corresponding to the second outlet (26); and
a locking device mounted between the base (10) and the cover (20) to attach the cover (20) to the base (10).

2. The photoelectrochemical detector as claimed in claim 1, wherein the locking device comprises:
two locking posts (14) formed on and protruding from the top of the base (10) at opposite sides of the front end and each of the two locking posts (14) having
a hole; and
a ball-spring combination mounted in the hole and comprising
a retractable ball (186) retractably mounted in the hole in the locking post (14); and
a resilient member (1 84) mounted in the hole to push the retractable ball outward; and
two ball detents (23) defined at the front end of the cover (20) to correspond to the retractable balls (186) when the cover (20) is closed.

3. The photoelectrochemical detector as claimed in claim 2,
wherein the cover (20) further has two side cutouts defined respectively at opposite sides of the front end to correspond to the locking posts (14); and the two ball detents (23) are defined in the two side cutouts and align respectively with the retractable balls (186) in the locking posts (14).

4. The photoelectrochemical detector as claimed in claim 2, wherein each locking post (14) further has:
a threaded hole (142) defined through the locking post (14); and
a threaded rod (1 8) screwed into the threaded hole (142) and having
a bore (1 82) defined in the threaded rod (1 8) in which the retractable ball (186) is mounted; wherein each resilient element is (184) mounted inside the bore (182) in one corresponding thread rod (18) to press the retractable ball (186) to correspondingly engage and lock with one of the ball detents (23).

5. The photoelectrochemical detector as claimed in claim 3, wherein each locking post (14) further has:
a threaded hole (142) defined through the locking post (14);
a threaded rod (18) screwed into the threaded hole (142) and having a bore (182) defined in the threaded rod (18) in which the retractable ball (186) is mounted; and
wherein a resilient element (184) is mounted inside the bore (182) in one corresponding thread rod (18) to press the retractable ball (186) to correspondingly engage and lock with one of the ball detents (23).

6. The photoelectrochemical detector as claimed in claim 5,
wherein each resilient element is a spring.

7. The photoelectrochemical detector as claimed in claim 1, wherein the spacer in the cover (20) comprises a gasket seat (28) defined in the bottom of the cover (20); and a rectangular gasket (282) with the inner open area mounted in the gasket seat (28).

8. The photoelectrochemical detector as claimed in claim 1,
wherein the device further has a reference electrode (30) corresponding to the second outlet (26).

9. The photoelectrochemical detector as claimed in claim 8,
wherein the device further has an auxiliary electrode (40) corresponding to the first outlet (26).

10. The photoelectrochemical detector as claimed in claim 1, wherein the recess (12) is a dovetail recess; and the base (10) further has multiple grooves (102) defined in the sides of the base (10) to make the base easy to hold.

* * * * *